United States Patent
Reinersman et al.

(10) Patent No.: US 7,286,214 B2
(45) Date of Patent: Oct. 23, 2007

(54) METHOD AND PROGRAM PRODUCT FOR DETERMINING A RADIANCE FIELD IN AN OPTICAL ENVIRONMENT

(75) Inventors: Phillip N. Reinersman, Tampa, FL (US); Kendall L. Carder, St. Petersburg, FL (US)

(73) Assignee: University of South Florida, Tampa, FL (US)

( * ) Notice: Subject to any disclaimer, the term of this patent is extended or adjusted under 35 U.S.C. 154(b) by 444 days.

(21) Appl. No.: 10/925,854

(22) Filed: Aug. 25, 2004

(65) Prior Publication Data
US 2005/0046828 A1    Mar. 3, 2005

Related U.S. Application Data

(60) Provisional application No. 60/497,666, filed on Aug. 25, 2003.

(51) Int. Cl.
*G01N 21/47* (2006.01)
*G06J 15/50* (2006.01)
*G01J 1/42* (2006.01)

(52) U.S. Cl. .................. 356/214; 345/426; 250/372

(58) Field of Classification Search ............. 356/214, 356/300–317; 250/372, 253; 702/22, 30, 702/167; 364/525; 345/426, 419, 423
See application file for complete search history.

(56) References Cited

U.S. PATENT DOCUMENTS

| | | | |
|---|---|---|---|
| 4,855,903 A * | 8/1989 | Carleton et al. ............ 709/248 |
| 5,296,711 A * | 3/1994 | Leonard et al. ............ 250/372 |
| 5,424,843 A | 6/1995 | Tromberg et al. |
| 5,454,068 A * | 9/1995 | Ramanujam ................ 345/419 |
| 5,867,807 A * | 2/1999 | Yamada et al. .............. 702/30 |
| 5,926,773 A * | 7/1999 | Wagner ...................... 702/22 |
| 6,076,010 A | 6/2000 | Boas et al. |
| 6,148,226 A | 11/2000 | Painchaud et al. |
| 6,157,037 A | 12/2000 | Danielson |

(Continued)

OTHER PUBLICATIONS

A. Tycho, T.M. Jorgensen, H.T. Yura, and P.E. Andersen, "Derivation of a Monte Carlo method for modeling heterodyne detection in optical coherence tomography systems," Appl. Opt. 41, 6676-6691 (2002).

R.J. Pahl and M.A. Shannon, "Analysis of Monte Carlo methods applied to blackbody and lower emissivity cavities," Appl. Opt. 41, 691-699 (2002).

(Continued)

*Primary Examiner*—Sang H. Nguyen
(74) *Attorney, Agent, or Firm*—Howard & Howard Attorneys, P.C.

(57) ABSTRACT

A hybrid method is presented by which Monte Carlo techniques are combined with iterative relaxation techniques to solve the Radiative Transfer Equation in arbitrary one-, two- or three-dimensional optical environments. The optical environments are first divided into contiguous regions, or elements, with Monte Carlo techniques then being employed to determine the optical response function of each type of element. The elements are combined, and the iterative relaxation techniques are used to determine simultaneously the radiance field on the boundary and throughout the interior of the modeled environment. This hybrid model is capable of providing estimates of the under-water light field needed to expedite inspection of ship hulls and port facilities. It is also capable of providing estimates of the subaerial light field for structured, absorbing or non-absorbing environments such as shadows of mountain ranges within and without absorption spectral bands such as water vapor or $CO_2$ bands.

17 Claims, 12 Drawing Sheets

U.S. PATENT DOCUMENTS

| | | | |
|---|---|---|---|
| 6,228,664 | B1 | 5/2001 | Bronson et al. |
| 6,256,367 | B1 | 7/2001 | Vartanian |
| 6,332,093 | B1 | 12/2001 | Painchaud et al. |
| 6,549,854 | B1 * | 4/2003 | Malinverno et al. .......... 702/16 |
| 6,549,861 | B1 | 4/2003 | Mark et al. |
| 6,820,032 | B2 * | 11/2004 | Wenzel et al. .............. 702/167 |
| 2002/0122570 | A1 | 9/2002 | Paragios et al. |
| 2002/0126129 | A1 | 9/2002 | Snyder et al. |
| 2003/0023172 | A1 | 1/2003 | Tromberg et al. |
| 2003/0053696 | A1 | 3/2003 | Schmidt et al. |
| 2003/0078503 | A1 | 4/2003 | Tsuchiya |
| 2003/0087641 | A1 | 5/2003 | Gustafsson |

OTHER PUBLICATIONS

C.D. Mobley, *Light and Water; Radiative Transfer in Natural Waters* (Academic Press, San Diego, Calif., 1994).

C.D. Mobley, B. Gentili, H.R. Gordon, Z. Jin, G.W. Kattawar, A. Morel, P. Reinersman, K. Stamnes, and R.H. Stavn, "Comparison of numerical models for computing underwater light fields," Appl. Opt. 32, 7484-7504 (1993).

P. N. Reinersman and K.L. Carder, "Monte Carlo simulation of the atmospheric point spread function with an application to correct for the adjacency effect," Appl. Opt. 34, 4453-4471 (1995).

P.N. Reinersman, K.L. Carder, and F.R. Chen, "Satellite-sensor calibration verification with the cloud-shadow method," Appl. Opt. 37, 5541-5549 (1998).

H.R. Gordon, "Ship perturbation of irradiance measurements at sea. 1: Monte Carlo simulations," Appl. Opt. 24, 4172-4182 (1985).

C.D. Mobley, *Hydrolight 4.1 User's Guide, First Printing* (Sequois Scientific, Inc., Redmond, Wash., 2000).

D.S. Burnett, *Finite Element Analysis* (Addison-Wesley Publishing Company, Reading, Mass., 1987).

K.L. Carder, C.C. Liu, Z. Lee, D.C. English, J. Patten, F.R. Chen, and J.E. Ivey, Illumination and turbidity effects on observing faceted bottom elements with uniform Labertian albedos, Limnol. Oceanogr. 48, 355-363 (2003).

C.D. Mobley and L.K. Sundman, "Effects of Optically shallow bottoms on upwelling radiances: Inhomogeneous and sloping bottoms," Limnol. Oceanogr. 48, 329-336 (2003).

* cited by examiner

METHOD AND PROGRAM PRODUCT FOR DETERMINING A RADIANCE FIELD IN AN OPTICAL ENVIRONMENT

RELATED APPLICATIONS

This patent application claims priority to and all advantages of U.S. Provisional Patent Application 60/497,666, which was filed on Aug. 25, 2003.

STATEMENT OF GOVERNMENT INTEREST

The work that led to this invention has been in supported in part by a grant from NASA, Grant Number NAS 5-31716. Thus, the United States Government may have certain rights to this invention.

FIELD OF THE INVENTION

The present invention generally relates to a method and program product for determining a radiance field in an optical environment. The present invention more specifically relates to a method and program product that applies Monte Carlo techniques to determine the radiance field in the optical environment.

BACKGROUND OF THE INVENTION

In the many fields of physical science in which researchers deal with aspects of radiative transfer, one important task is to determine the direction and intensity of radiant energy transport within a region of interest, given: 1) optical parameters describing the scattering and absorption characteristics of the optical media within the region; 2) the specification of the direction and intensity of radiant energy incident on the boundary of the region; and 3) the specification of any radiant source distribution within the region. For example, the development of optical coherence tomography techniques in the realm of medical optics requires knowledge of the response of new optical instruments.

Accurate calibration of blackbody sources used in pyrometry and spectroscopy requires determination of the emission characteristics of new experimental sources. Remote sensing of the earth's atmosphere, terrain and marine environments depends upon instruments, the design and calibration of which are possible only after the specification of the optical conditions in which the instruments are to perform. These specifications are frequently determined by simulation of the radiant energy transport in the physical conditions to be encountered by the instruments.

The process common to all three endeavors mentioned above, namely, the radiative transfer of energy through media capable of interacting with and altering the radiance field, is governed by the Radiative Transfer Equation or RTE. Unfortunately, the RTE supplies no analytic solution for problems characterized by realistic geometries, boundary conditions and optical parameters. As a result, the "solving" of the RTE for realistic optical environments consists currently of specifying the parameters necessary to define the problem, and then numerically simulating the solution, such as the radiance field, at the desired location(s).

Many methods for generating numerical solutions to the RTE in the optically coupled ocean-atmosphere environment have been developed in support of studies of the earth's atmosphere and oceans. Most of this environment can be represented by one-dimensional models that treat the atmosphere and oceans as stratified media that are horizontally infinite in extent and in which the optical parameters vary only with depth or height. Indeed, in the common case of clear sky over open ocean waters, the one-dimensional approximation is very good; the one-dimensional models execute quickly and have negligible or acceptable error. In order to operate effectively, a researcher or other person using monitoring equipment should be capable of establishing parameters for the particular environment and the conditions at the time of taking readings. Because these parameters are dynamic in nature, it is necessary to formulate a scenario for the conditions at the time of the instrumental measurements to determine the effectiveness of the results as well as the set up conditions for the instrumentation. This has been found to be possible in difficult media by using the Monte Carlo method which can give an accurate depiction of the magnitude of the measured entity for a given set of conditions. However, Monte Carlo calculations are also long and cumbersome in nature and require a great amount of data manipulation.

SUMMARY OF THE INVENTION AND ADVANTAGES

A method and program product for determining a radiance field in an optical environment are disclosed. The method includes generating a model of the optical environment and partitioning the modeled, optical environment into discreet, contiguous regions. The method further includes applying Monte Carlo techniques to determine an optical response function for each region for which the optical response function cannot be analytically defined. The program product includes codes for accomplishing the various steps associated with the method described above.

The method and program product of the present invention utilize Monte Carlo techniques to solve a Radiative Transfer Equation (RTE) in arbitrary one, two, or three-dimensional environments. The present invention permits the rapid determination of characteristics of an optical environment for a known and thus standard set of parameters. This enables a more efficient and finer processing of information to occur. From this information, it is possible to gain a perspective on the accuracy and actual ability of an optical instrument, such as a sensor, to perform an analysis for given conditions at any specific time.

More specifically, the method and program product of the present invention approximate the solution of the RTE in any dimension. To effect this approximation, the method and program product generate a model of the optical environment and partition the modeled, optical environment into discreet, contiguous regions and then solves the RTE in each element using Monte Carlo techniques. The output from each element then serves as the input to adjacent elements. Radiance from boundary and internal sources is diffused throughout the environment as the element outputs are readjusted iteratively. Once the iterative technique converges, the radiance is known on the boundary and throughout the entire modeled environment. The method of the present invention predicts the efficacy of instrumental measurements for a given set of conditions and provides a set of parameters for given situations which may be used to predict the outcome and error probabilities for those conditions.

BRIEF DESCRIPTION OF THE SEVERAL VIEWS OF THE DRAWINGS

Figure 1:
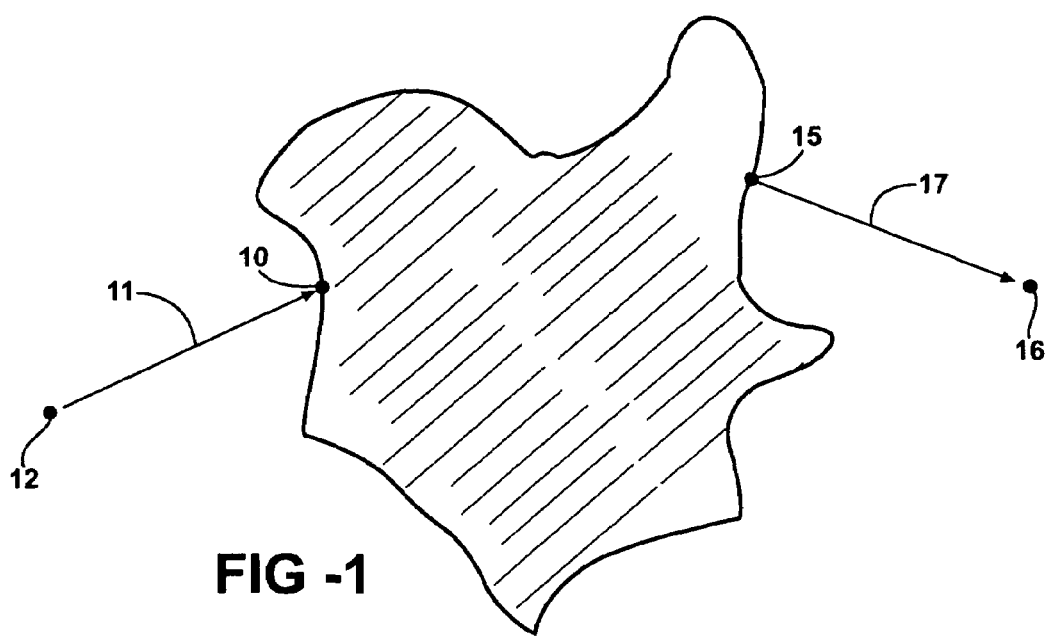

Having thus described the invention in general terms, reference will now be made to the accompanying drawings, which are not necessarily drawn to scale, and wherein:

FIG. 1 depicts the transmission of irradiance into and out of a region of interest, according to an illustrative example of the present invention.

Figure 2:
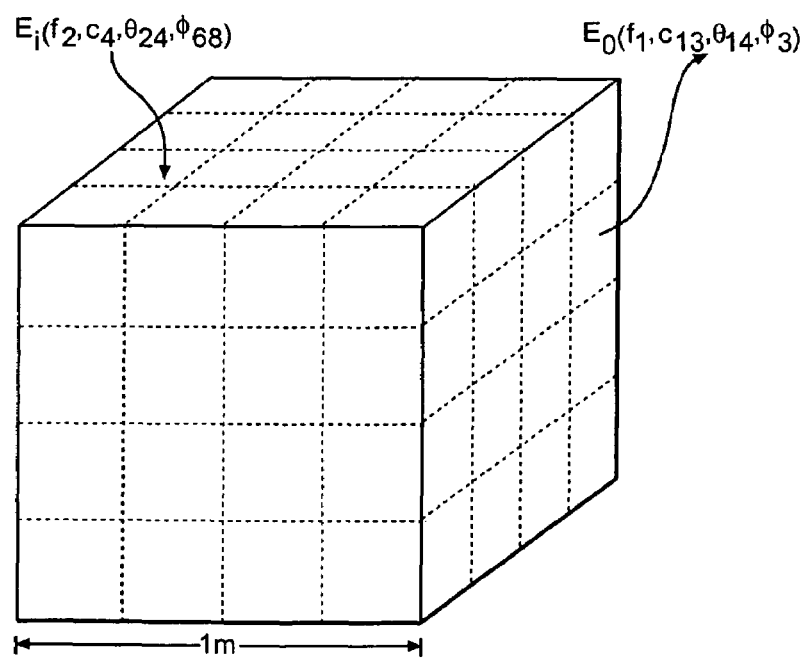

FIG. 2 shows a 3-D cubic structure with each face subdivided into 16 grid cells, according to an illustrative example of the present invention.

Figure 3:
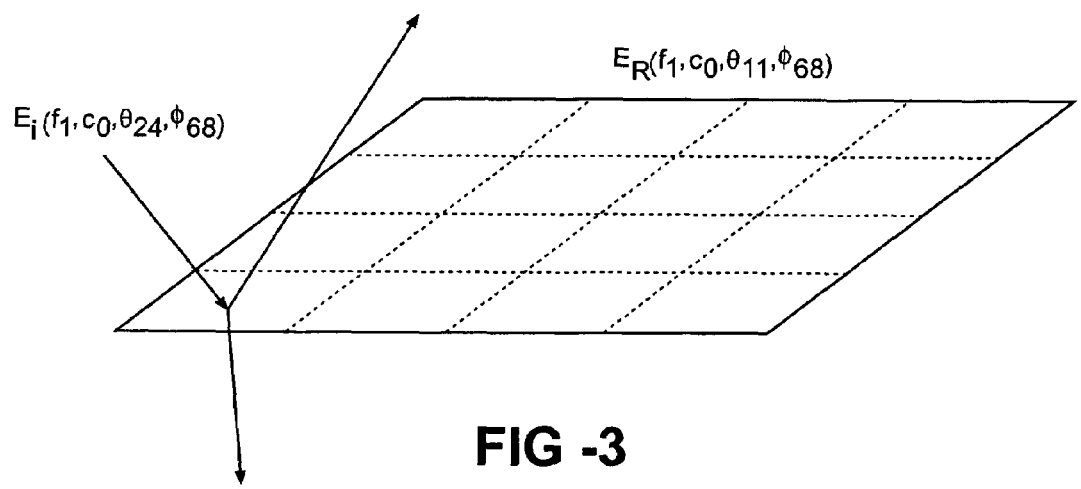

FIG. 3 is a 2-D plate, according to an illustrative example of the present invention.

Figure 4:
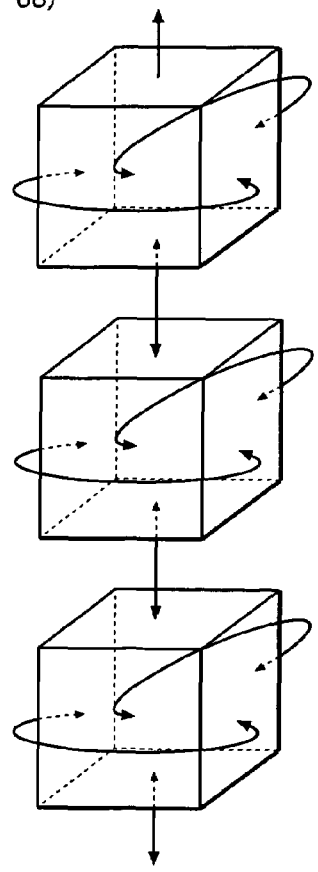

FIG. 4 shows the modeling of one dimensional environments using three-dimensional cubes, according to one aspect of the present invention.

Figure 5:
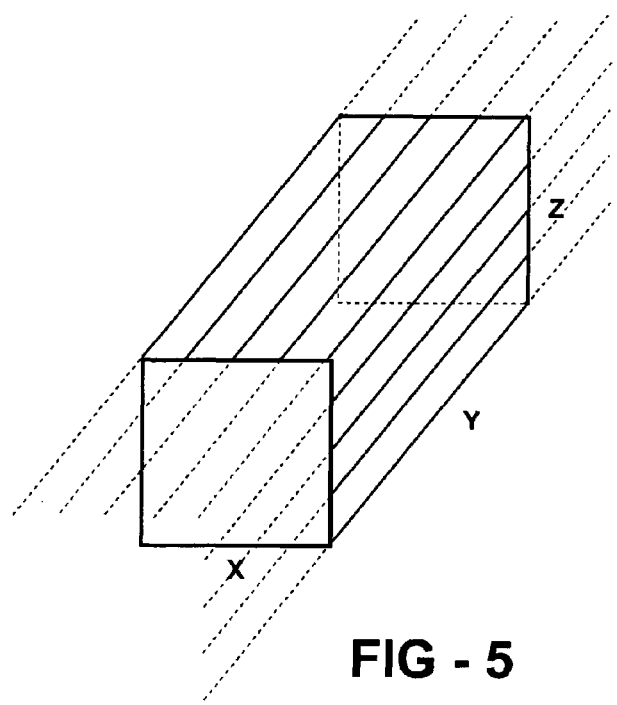

FIG. 5 shows the modeling of an infinitely long bar of square cross-section, according to one aspect of the present invention.

Figure 6:
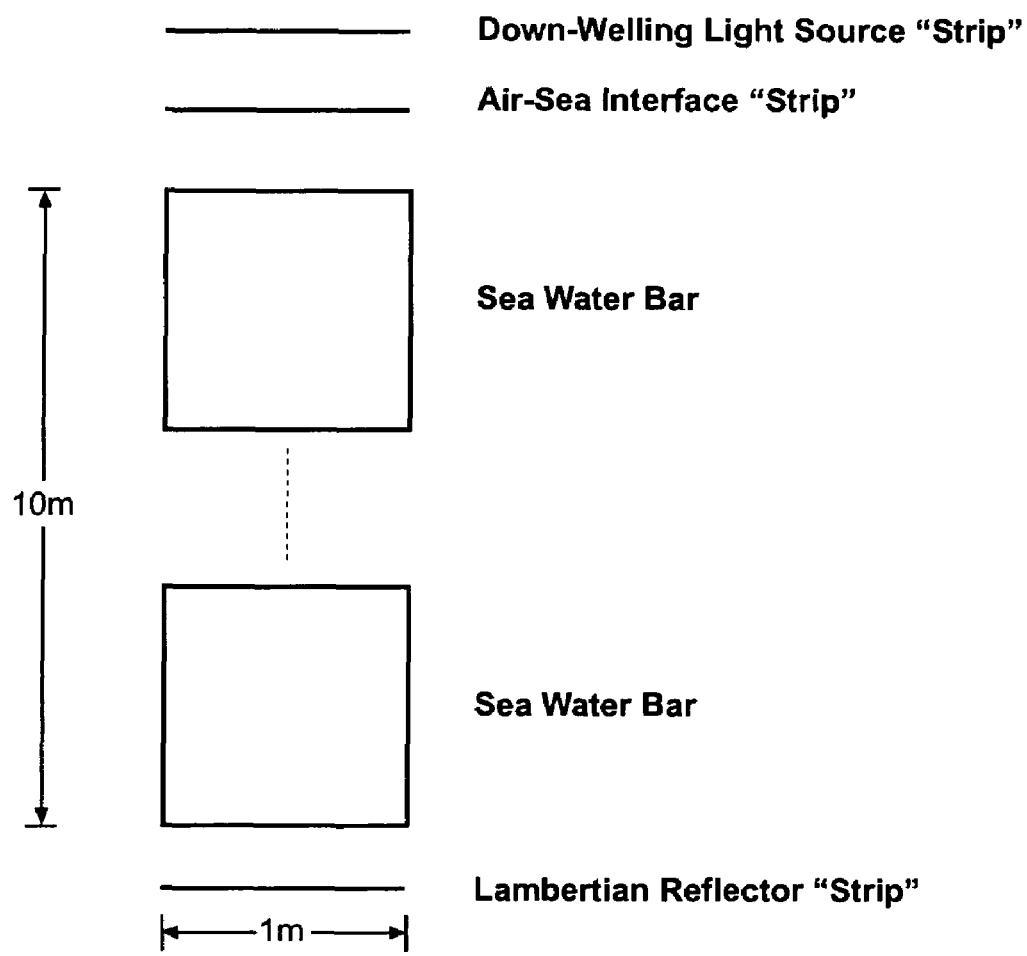

FIG. 6 shows a model geometry for solving a 1-dimensional problem using long bars and strips, according to one aspect of the present invention.

Figure 7:
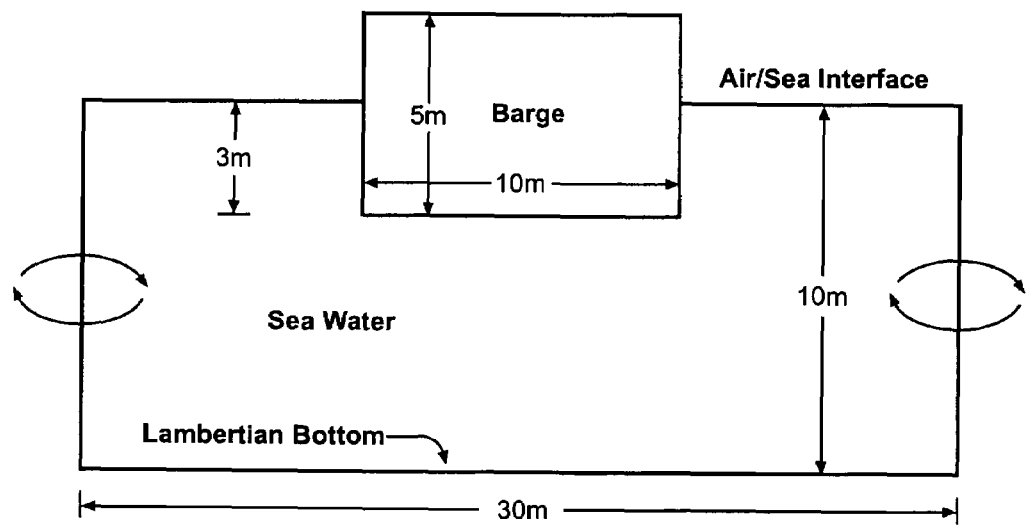

FIG. 7 shows a model geometry for solving a 2-dimensional problem, according to one aspect of the present invention.

Figure 8:
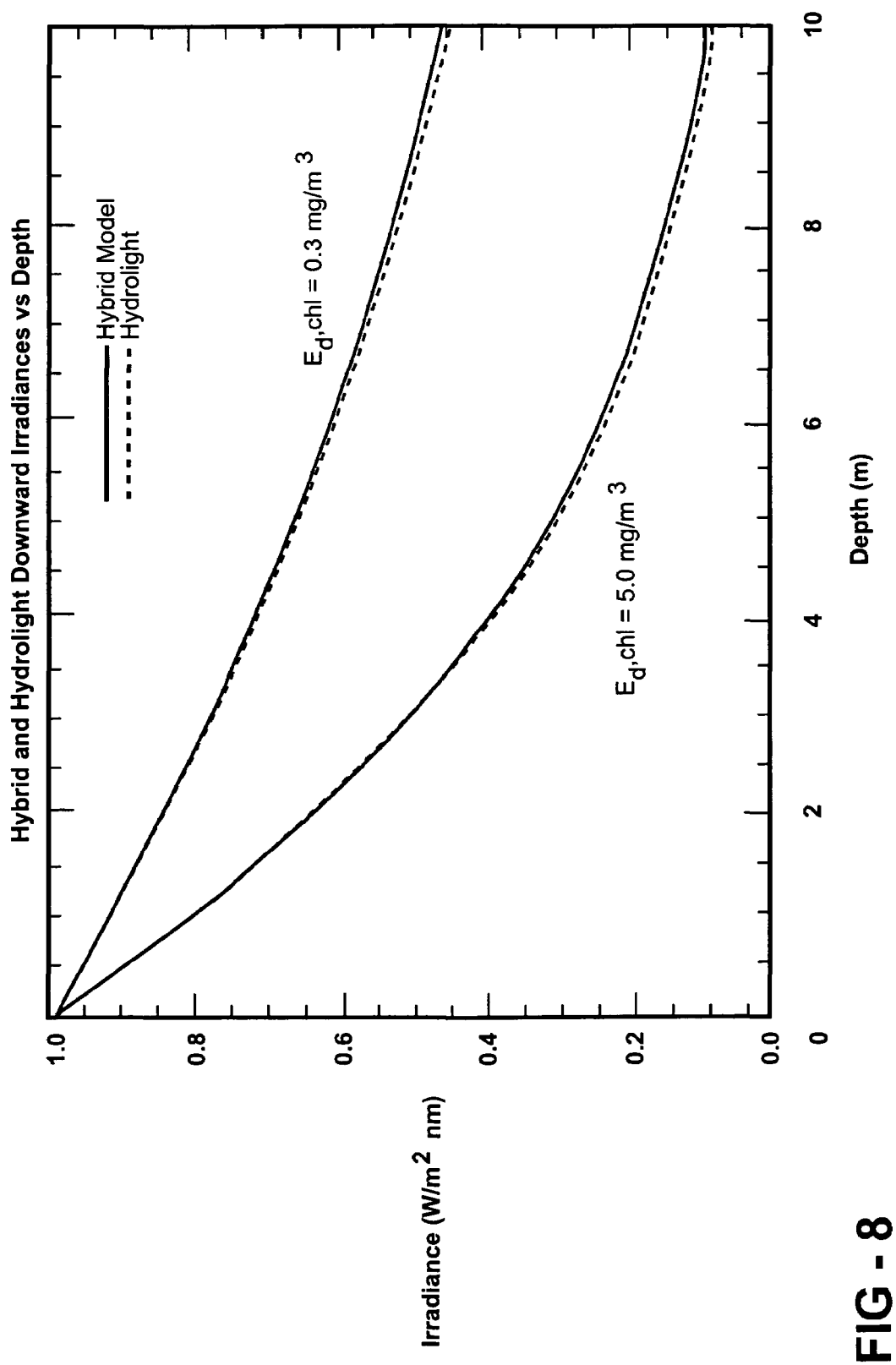

FIG. 8 illustrates the downward irradiance ($E_d$) vs. depth as calculated by the methods of the present invention and by Hydrolight, according to one illustrative example.

Figure 9:
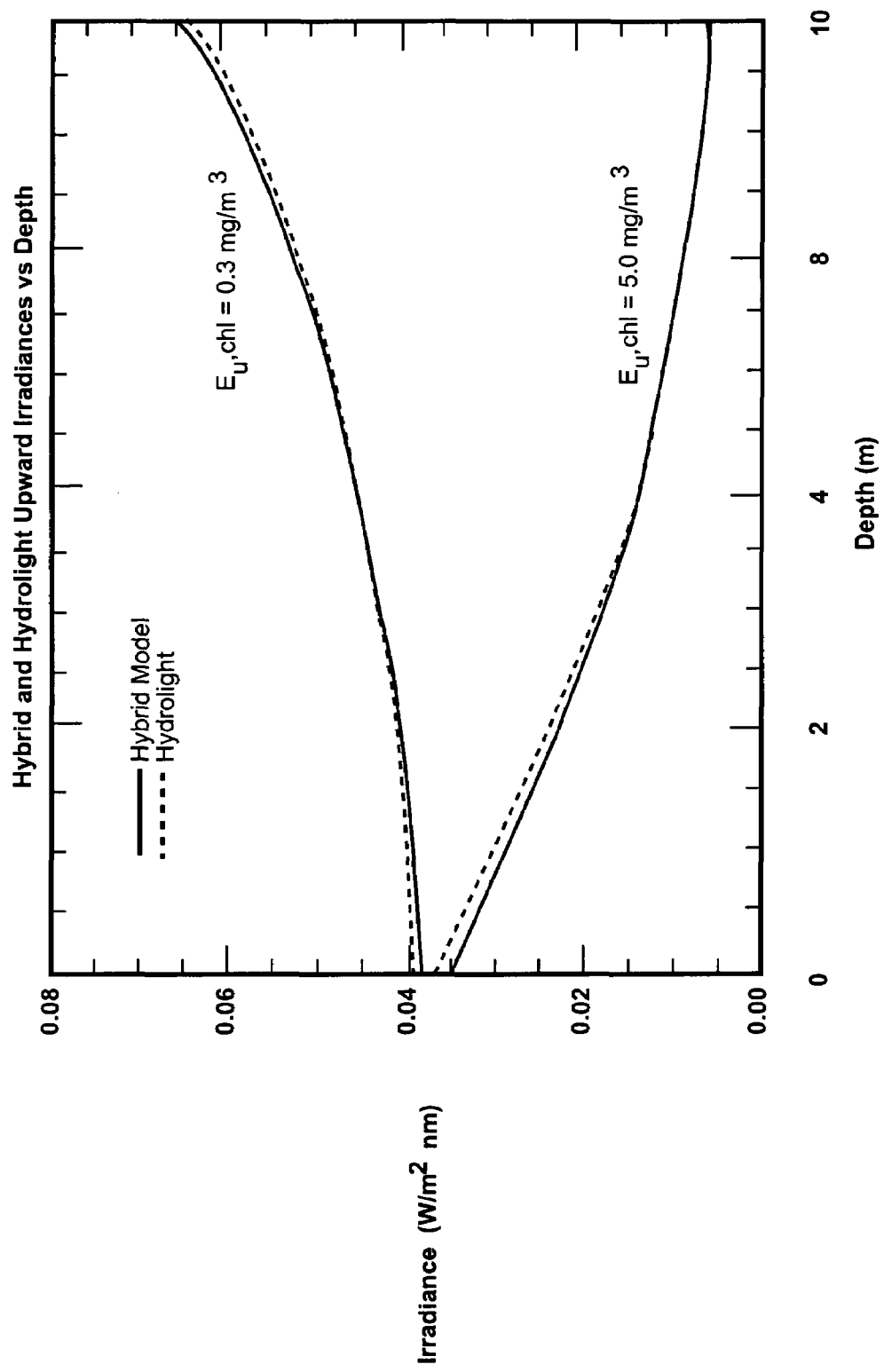

FIG. 9 illustrates the upward Radiance ($E_u$) vs. depth as calculated by the methods of the present invention and by Hydrolight, according to one illustrative example.

Figure 10:
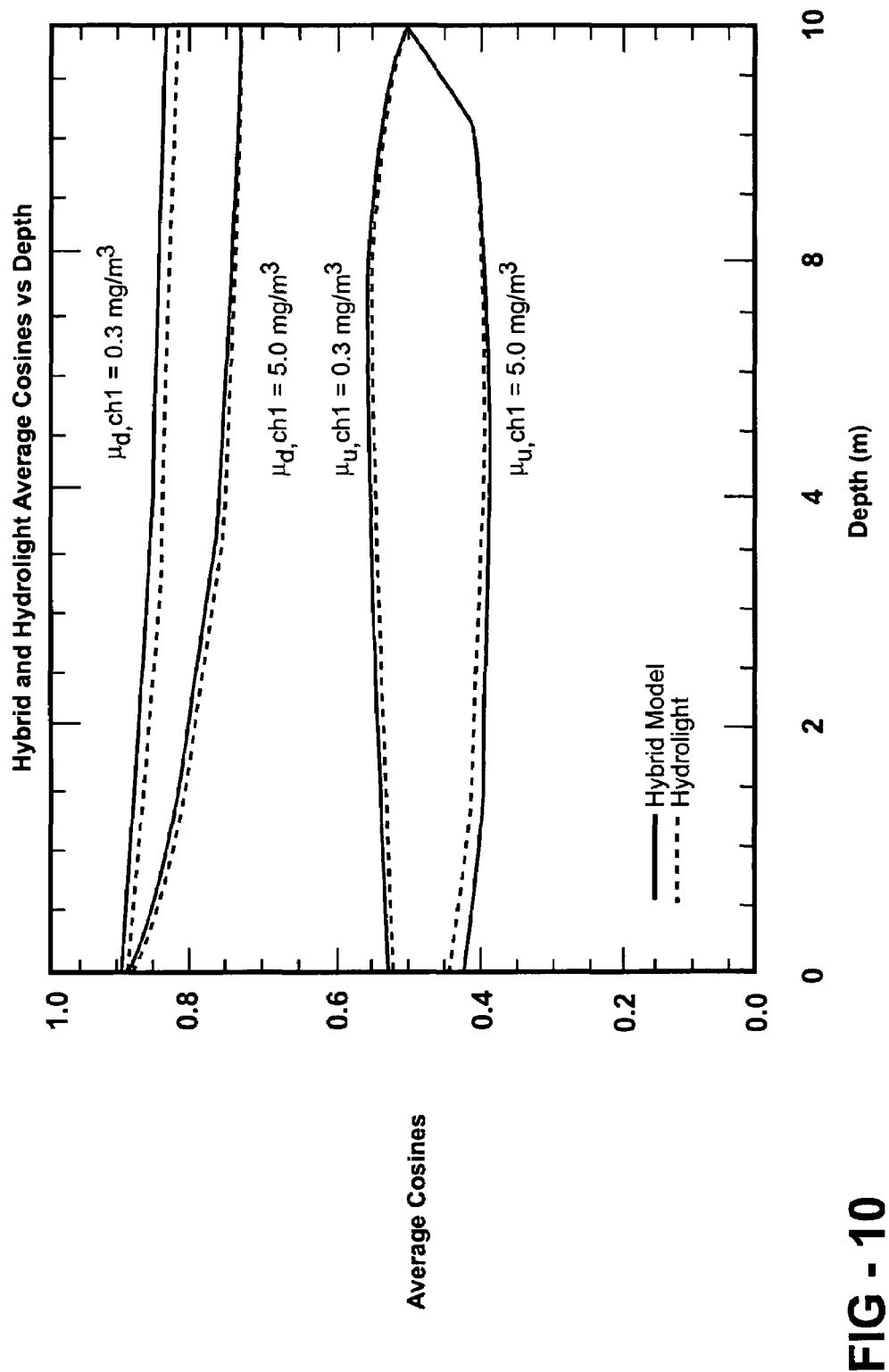

FIG. 10 shows the average cosines plotted vs. depth as calculated by the methods of the present invention and by Hydrolight, according to one illustrative example.

Figure 11:
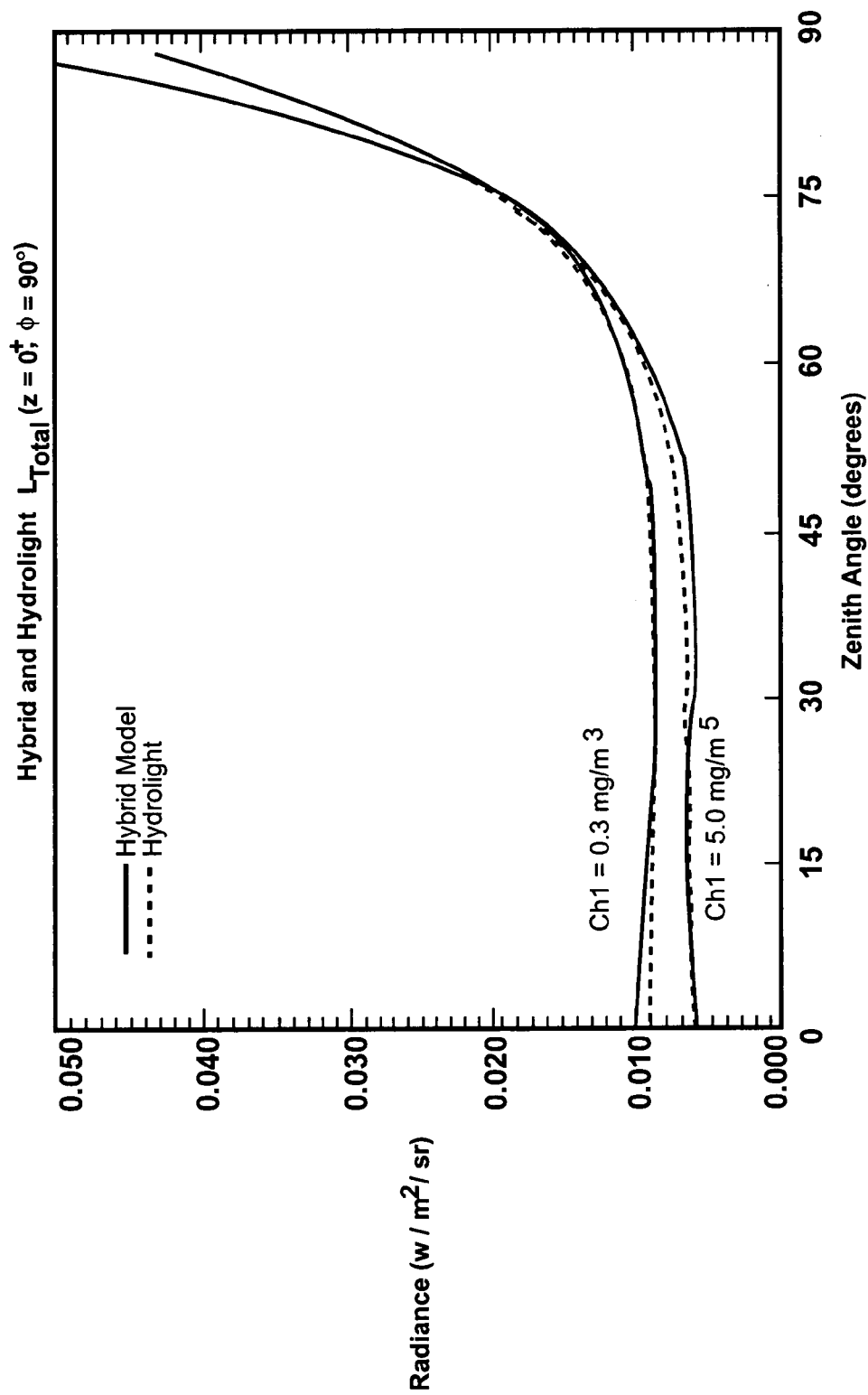

FIG. 11 shows the total upward radiance just above the surface in the half-plane perpendicular to the principal plane as calculated by the methods of the present invention and by Hydrolight, according to one illustrative example.

Figure 12:
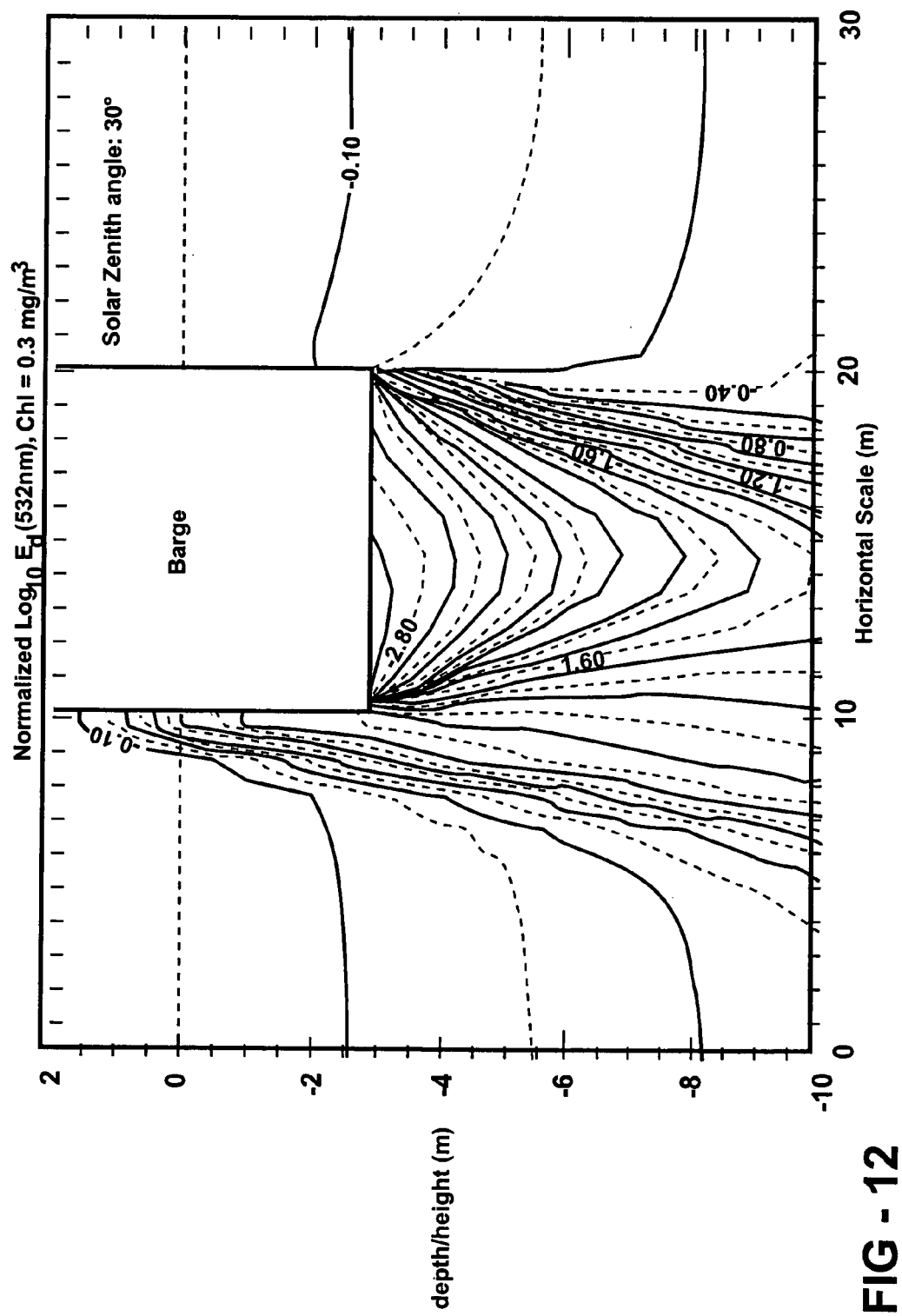

FIG. 12 shows an illustrative normalized $Log_{10}E_d$ at 532 nm, Ch1=0.3 mg/m$^3$ as calculated by the methods of the present invention.

Figure 13:
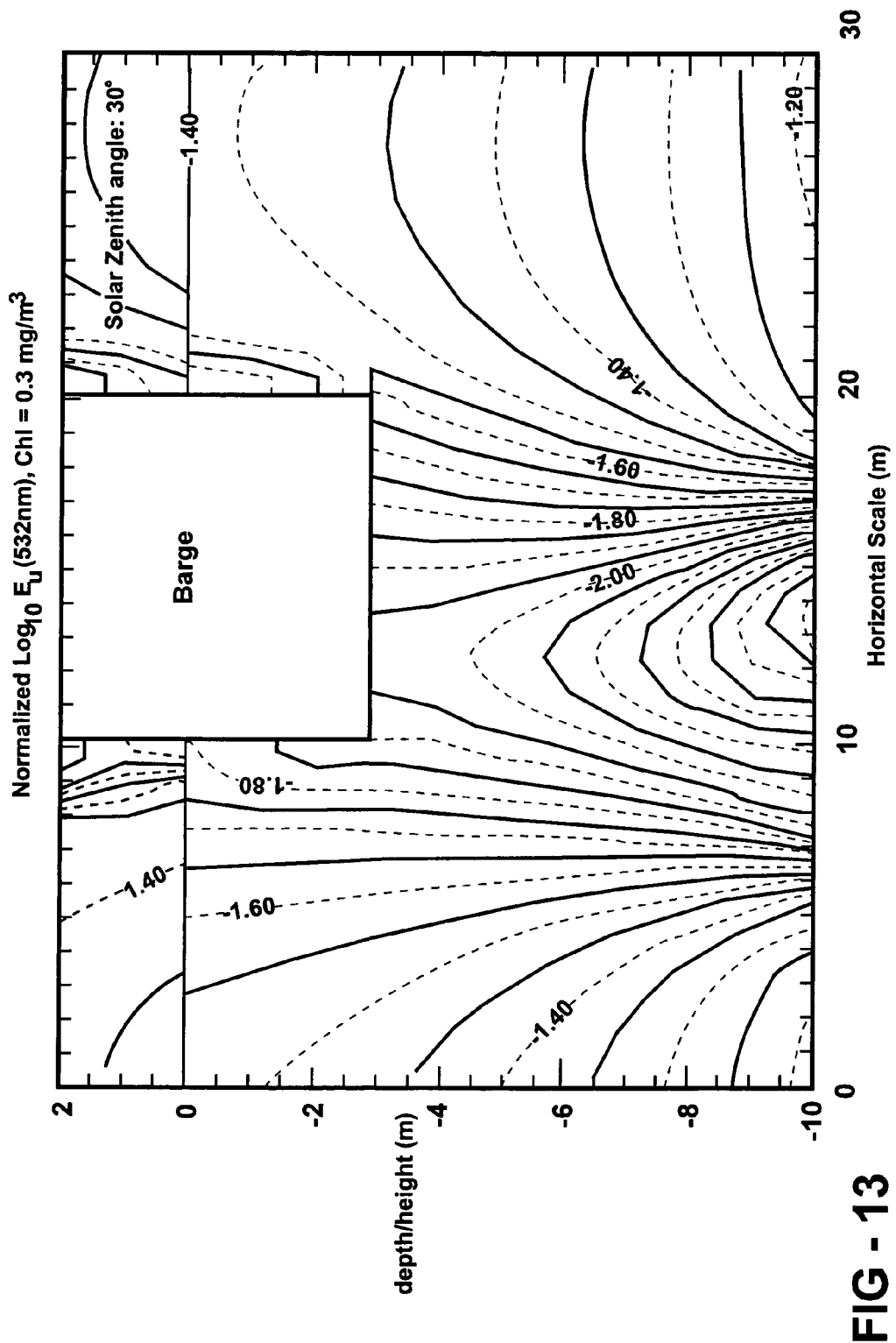

FIG. 13 shows another illustrative normalized $Log_{10}E_u$ at 532 nm, Ch1=0.3 mg/m$^3$ as calculated by the methods of the present invention.

Figure 14:
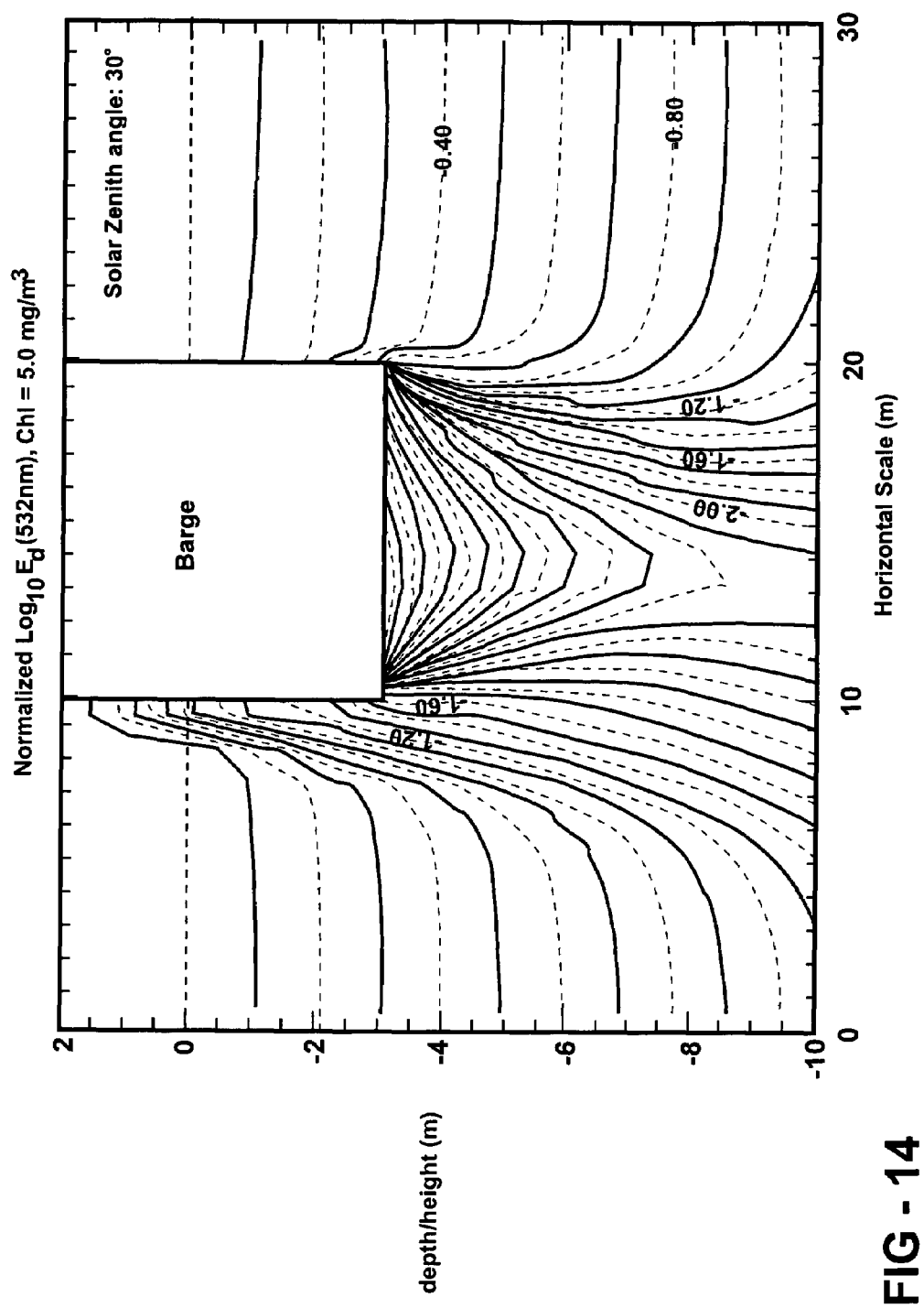

FIG. 14 shows an illustrative normalized $Log_{10}E_d$ at 532 nm, Ch1=5.0 mg/M$^3$ as calculated by the methods of the present invention.

Figure 15:
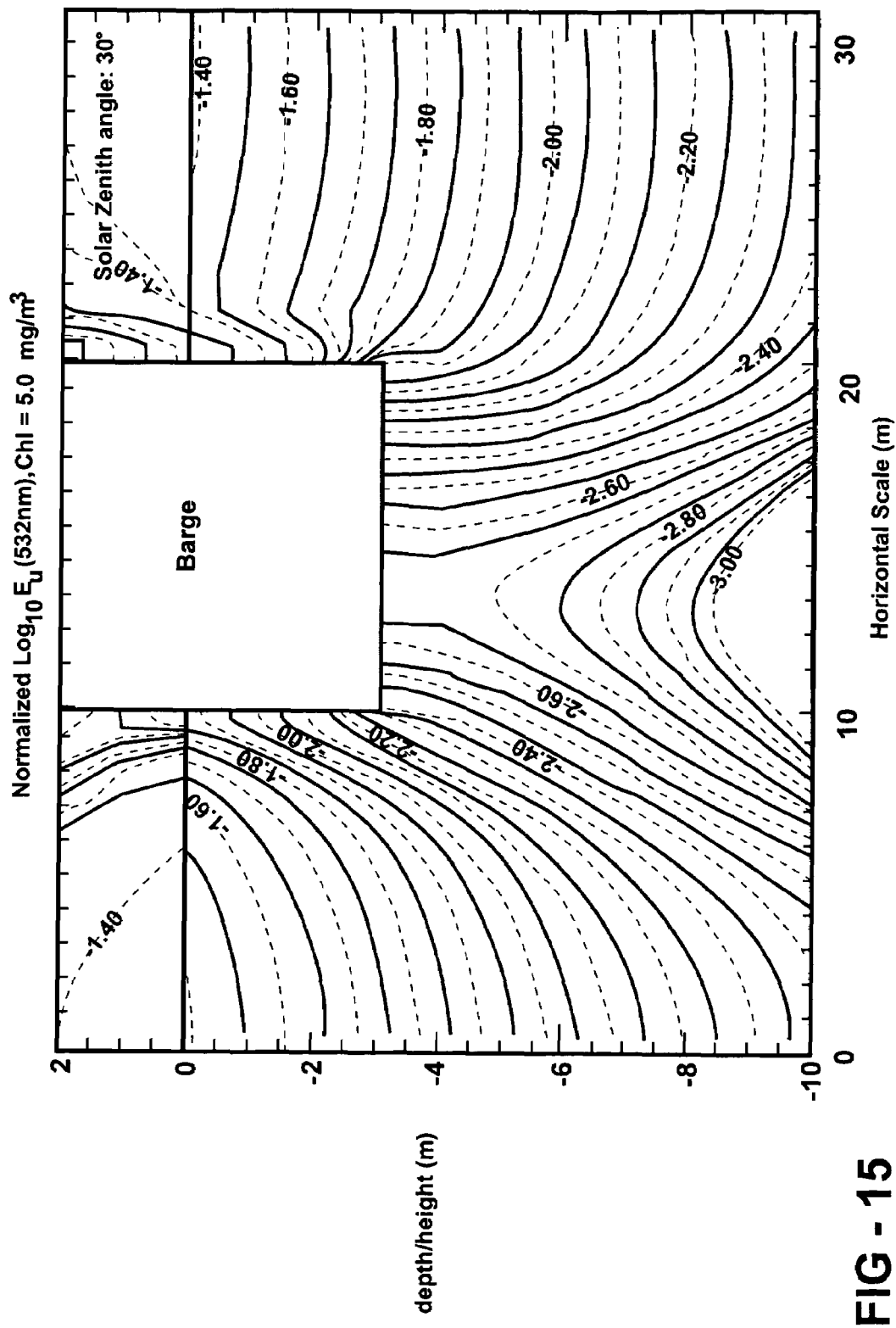

FIG. 15 shows an another illustrative normalized $Log_{10}E_u$ at 532 nm, Ch1=5.0 mg/m$^3$ as calculated by the methods of the present invention.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The present invention includes a method and program product for determining a radiance field in an optical environment. Generally, the method and program product generate a model of the optical environment, partition the modeled, optical environment into discreet, contiguous regions, or elements, and apply Monte Carlo techniques to determine an optical response function for each region for which the optical response function cannot be analytically defined. The optical response function provides an output for any given input. The step of applying Monte Carlo techniques to each region more specifically comprises solving the Radiative Transfer Equation (RTE) for each region to obtain an end solution indicative of the radiance field in the optical environment.

Those skilled in the art readily recognize that there is not 'one' RTE. Instead, there are many different forms of the RTE but, generally, the RTE is the equation which describes the propagation of radiation (e.g. light) through a scattering and absorbing medium. Radiation and light are used interchangeably herein. However, it is to be understood that light is but one form of radiation and, in a general context, radiation refers to any type of electromagnetic radiation.

For the purposes of the present invention, the terminology optical environment is directed at any environment, or region of space, that is desirable to model where particular attention is paid to optical properties of the environment including, but not limited to, scattering and absorption characteristics. Non-limiting examples include the optical environment underwater or subaerial. Further, it is understood by those skilled in the art that the optical response for some regions can be analytically defined. As such, application of the Monte Carlo techniques is not required toward these particular regions. In other words, the Monte Carlo techniques do not have to be applied to each region that has been partitioned.

The method and program product further include combining the optical response function for each region. Further, the output of one region is utilized as an input to a contiguous region. The output of one region, therefore, depends on the input into the same region, as well as the optical response function. Preferably, iterative relaxation techniques are then applied to determine the radiance field on a boundary and throughout the modeled, optical environment. In this context, the outputs from each region are iteratively adjusted. Due to the application of the iterative relaxation techniques, the present invention is a hybrid method that includes two primary phases, (1) application of the Monte Carlo techniques followed by (2) application of the iterative relaxation techniques. The program product of the present invention includes specific codes, such as a modeling code, a partitioning code, an application code, a combination code, and a relaxation code for accomplishing the various steps associated with the method described above.

The method of the present invention includes many different practical applications in response to obtaining the end solution. For instance, the method may calibrate data from an optical sensor in response to the end solution. As described additionally below, the calibration of the data may include adjusting gain of the optical sensor, preferably automatically, in response to the end solution. The method may validate data from an optical sensor in response to the end solution. Further, the method may determine a particular optical sensor to deploy in response to the end solution. Even further, the method may adjust an optical sensor in response to the end solution prior to deployment of the optical sensor. As alluded to above, the term optical sensor is used interchangeably with optical instrument. In any event, although not required, it is preferred that the optical sensor is located on at least one of a remotely operated vehicle (ROV), an autonomous underwater vehicle (AUV), a piloted aircraft, an autonomous aircraft, a semi-autonomous aircraft, a piloted spacecraft, an autonomous spacecraft, and a semi-autonomous spacecraft. Further, it is to be understood that the terminology spacecraft includes satellites.

In the field of instrumental analysis, many calibration methods are based on one-dimensional models. These models fail, since in the case of field observations, the world is not one-dimensional in nature. In fact, the efficiency of the instrument is dependent of the environmental parameters encountered in the field. Some examples of this include the radiance received at a spaceborne sensor viewing coastal areas where relatively dark water adjoins bright beaches, or viewing maritime scenes in the presence of brightly reflecting clouds. One-dimensional models also fail when the geometry of the region to be modeled is not one-dimensional in nature, such as when modeling the light field adjacent to and beneath a ship.

Monte Carlo techniques comprise the only known method of solving the RTE for those problems not amenable to the one-dimensional approximation. The radiance distribution in any region, including those with irregular geometries, parameter distributions, and boundary conditions, may be modeled by Monte Carlo methods. Furthermore, the solution to the RTE in any region may be achieved to any desired degree of accuracy and may also be collated for a prescribed set of conditions. Thus Monte Carlo packages or modules for differing conditions may be formulated for those conditions and then may be used to predict the efficiency of instrumentation or the reliability of results for any set of conditions. In this way, an operational package or Monte Carlo code may be produced for the study conditions for a set of circumstances.

In general, there are three serious disadvantages of Monte Carlo methods. First, for the most part, Monte Carlo models do not execute quickly. Monte Carlo techniques require the accumulation of statistics based on tracing the histories of vast numbers of photons from their source to their extinction or lack of relevance. The process involves repeated sampling of probability distributions to determine the type and outcome of events the photons undergo. In realistic three-dimensional regions the ray-tracing routines necessary to calculate the path of the photons, their intersections with objects and boundaries, and their reflections and refractions, can become computationally burdensome. Therefore, Monte Carlo codes may require hours, days, or even weeks to execute, depending on geometric complexity and the quantity of interest.

Second, Monte Carlo codes are generally problem specific in nature. Although some subroutines, such as those determining path length or scattering angle, may be reusable, most "new" problems require extensive coding and testing. Once the new code compiles and executes correctly, it may be difficult to verify the model results, since, in theory, the model is simulating a scenario for which no other model exists and no physical measurements are available.

Third, Monte Carlo models generally provide results for only one set of optical parameters at a time, and at once, or at most, a few, locations within a modeled region. To change optical parameters or to move the location of the model sensor system usually requires rerunning of the model.

For these reasons, at least within the context of atmosphere/ocean remote sensing, Monte Carlo techniques are most often employed to solve the RTE in two- or three-dimensional situations for which the faster techniques are not applicable. Monte Carlo solutions for these cases may be used to determine the accuracy of one-dimensional models when they are applied to two- or three-dimensional scenarios. Once the errors are quantified, corrections to one-dimensional models may be developed that allow the models to be applied to environments that are perturbed from one-dimensional in specific ways, such as for sloped or patched sea floors underlying an otherwise one-dimensional water column.

Methods and computer program products of the present invention approximate the solution of the RTE in any dimension. To effect this approximation, the methods and computer program products of the present invention partition a model environment into contiguous regions, or elements, and solve the RTE in each element using Monte Carlo techniques. The output from each element then serves as the input to adjacent elements. Radiance from boundary and internal sources is diffused throughout the environment as the element outputs are readjusted iteratively. Once the iterative technique converges, the radiance is known on the boundary and throughout the entire modeled environment.

The advantages of the instant method stem from the reuse of basic environmental elements, and from the ease with which the elements may be combined to form new geometries. Furthermore, once a particular environment is modeled, the time required to solve for a similar environment is substantially reduced.

It will be appreciated that the methods of the present invention are described below with reference to block diagrams. It will be understood that each method described below can be implemented by computer program instructions. These computer program instructions may be loaded onto one or more general purpose computers, special purpose computers, or other programmable data processing apparatus to produce machines, such that the instructions which execute on the computers or other programmable data processing apparatus create means for implementing the functions specified in the flowchart block or blocks. Such computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. Therefore, the methods described herein may be implemented by a modeling tool comprising a processor, operating system, memory, input/output interface, one or more databases and a bus.

Further, the methods described herein may be embodied as a data processing computer-readable program code means embodied in the storage medium. Any suitable computer-readable storage medium may be utilized including hard disks, CD-ROMs, DVDs, optical storage devices, or magnetic storage devices. Accordingly, the present invention may take the form of an entirely hardware embodiment, an entirely software embodiment or an embodiment combining software and hardware aspects, such as firmware. According to a preferred embodiment, die methods described herein are implemented by a stand-alone software application operating on a Windows® operating system. However, the methods may be implemented using alternative operating systems and databases as are known to those of skill in the art.

Referring now to FIG. 1, methods of the present invention consider a point, 10, on the surface of an arbitrary region. This point 10, is illuminated by a beam of radiant power, 11, at wavelength $_2$ and from direction 12. $E_i$ is that portion of the irradiance at point 10 that arrives from direction 12 and is expressed in units W m$^{-2}$sr$^{-3}$. As a result of this illumination, power may be emitted from the region at $_o$ point 15, along direction 17 toward detector 16.

The linearity of the RTE implies that the amount of energy leaving the region at point 15 and in direction 17 resulting from the energy at point 10 from direction 12 is proportional to the amount of energy at point 10 from direction 12. The point-by-point constant of proportionality is denoted as the "response function" and is defined as:

$$E_o(\rho_o,\epsilon_o;E_i(\rho_i,\epsilon_i))=R(\rho_o,\epsilon_o;\rho_i,\epsilon_i)E_i(\rho_i,\epsilon_i).$$

If R is known for all points on the boundary of the region, and for all directions, then the power emitted by the region is completely determined by the incident power distribution. The total power emitted from differential of the surface area centered on point 15 and propagating within the differential cone of directions centered on direction 16 is given by:

$$E_o(\rho_o,\epsilon_o)dA(\rho_o)d\Omega(\epsilon_o)=\int\int_{d\Omega} R(\rho_o,\epsilon_o;\rho_i,\epsilon_i)E_i(\rho_i,\epsilon_i)dA$$

The integrals in the above equation are expressed over the entire boundary of the region and all directions, $d\Omega$, which are incident on the region at $dA$.

The relationships given in the above equations are useful for Monte Carlo techniques and have two properties. First, R is a relationship between points on the surface of the region and is not explicitly dependent on the optical media within. R depends on the material within the region. But when R can be measured, deduced, or defined for the region, when the power distribution incident on the surface of the region is known, the emitted power distribution can be calculated without further reference to the optical properties of the region. Secondly, there are regions for which R is known or may be defined exactly. These include regions within which no scattering takes place and regions with boundaries that have known reflectance characteristics.

Constructing A Model

The first step in creating a simulation of the light field in a given optical environment is to partition the environment into discreet, contiguous elements in a similar manner as is employed in a finite element analysis. Two element shapes may be used to illustrate the methods of the present invention: the three-dimensional cube as shown in FIG. 2 and the two-dimensional square plate depicted in FIG. 3. It will be appreciated that their shapes are for illustrative purposes only, and are non-limiting examples.

In the illustrative example shown in FIG. 2, the 3-D cube has a directional resolution of 5°×5° with an input at face 2, cell 4, theta bin 24 and phi bin 68. Generally, a cube may be used to represent a three-dimensional region of the model environment containing a well-defined distribution of optically reactive constituents such as seawater, particulates, etc. Once the RF is calculated for this particular distribution of optical agents, that RF may be used repeatedly for other cubic regions of the model environment that contain the same constituent distributions.

The illustrative plate shown in FIG. 3 represents a Fresnel interface with the reflected ($E_R$) and transmitted ($E_T$) irradiance results from an input $E_i$. The plate may be used to represent, e.g., boundaries, interfaces, and sources. In this way, one or more plates may be used to represent the sea floor, the bottom and sides of barges, and/or an air/sea interface. Plates may also be used to represent the upper boundary of a modeled environment, such as a source with a radiance distribution representing the solar beam and skylight.

The spatial resolution of a model depends on the resolution of the special grid imposed on the surface of the elements as depicted in FIGS. 2 and 3. Each output value of the element is an average over the area of the grid with which it is associated. Therefore, it is expected that the grid resolution should be small compared to the scale of spatial change of the expected modeled light field. For instance, a smaller grid size may be required to model the area near the air/sea interface than is required to model a region in deep, homogeneous water. In addition the size of the model (e.g., a chosen cube structure such as that shown in FIG. 2) may be selected to replicate sizes of the physical shapes found in the proposed model environment. As in FEM where a problem may be solved repeatedly, increasing resolution until the result converges, may also be employed here.

Referring to FIG. 2 as an illustrative and non-limiting example, a grid size of 0.25 m may be deemed appropriate. This grid resolution is achieved by partitioning the faces of a 2 m cube as shown (into 64 identically-sized smaller cubes), or by modeling 0.25 m cubes with only 1 grid cell per face. The optimal choice will, of course, be problem specific, and involves trade offs between computational efficiency, error tolerance, and data requirements as discussed in detail below. In any event, the size of cube chosen should be small enough to allow the model to approximate the physical shapes found in the modeled environment.

Similar considerations apply to the determination of the directional resolution of the model. Monte Carlo simulations of radiative transfer generally partition a directional sphere onto discreet regions referred to as averaging quads or directional bins, reflecting the fact that the simulations do not keep track of the direction of each photon to pass the detection point, but instead simply increment the count of the appropriate directional bin. Customarily, the directional sphere is partitioned into quads bounded by circular arcs of constant polar angles (latitude) and circular arcs of constant azimuthal angles (longitude). The longitude lines are generally evenly spaced, dividing the sphere into equally sized lines. The latitude lines may be drawn so that for all latitude lines, the difference in polar angles between any two adjacent latitude lines is constant, or so that the difference in the cosine of the polar angles between any two adjacent latitude lines is constant. In either case, the triangular regions at the poles are often combined to form polar caps.

According to the present invention, the former approach is preferred such that the triangular sections of the sphere are not combined into polar caps. This procedure results in bins in which the subtended solid angle varies depending on the polar angle of the bin. Bins near the sphere equator are larger, and this may be expected to result in collection of more "counts" than bins at the polar regions, implying that for any given Monte Carlo run, the values averaged over the equatorial bins will be more reliable than those averaged bins closer to the poles. This situation may be remedied by employing the latter method to draw latitude lines, but then the polar quads may be elongated compared to those nearer the Equator. Thus, two numbers are required to identify a directional bin; one to identify the polar zone, the theta bin number, and another to identify the azimuthal zone angle, or phi bin number. Thus, the raw output value for a face f, grid cell c, theta bin t, and phi bin p, denoted as $O_r(fc,t,p)$ is the total number of photons passing through face f, jgrid cell c, and the directional bin formed by the intersection of theta bin t and phi bin p.

Once the spatial and directional resolutions are decided upon the memory requirements of the model are preferably checked to confirm that they remain tractable, though this is not required according to one aspect of the present invention. One example is the memory requirements for the Monte Carlo modeling of the RF for the illustrative cube of FIG. 2. One copy of the RF will have $((6\times16\times36\times72)/2)^2=15{,}479{,}341{,}056$ data values, each of which requiring 8 bytes for double precision calculations, which may exceed the performance abilities of many computers.

Because the hybrid model approach can be tested on 1-dimensional and 2-dimensional environments without loss of generality, the size of the RF's can be reduced substantially. For example, if a 1-dimensional environment is to be modeled at the resolution shown in FIG. 2, one method of constructing the model is to stack 3-dimensional cubes in a column as shown in FIG. 4. Then, the output from the front face of the cube may serve as the input to the back face, and vice versa. The output from the left face of the cube serves as the input to the right face, and vice versa. This is referred to as wrapping. Similarly, the output from the top face of a cube serves as the input to the bottom face of the cube above it, and vice versa. Even if all the cubes represent optically identical parcels, the full Monte Carlo model of the RF will be required. Then, for the iterative phase of the model, one copy of the RF and one copy of the output state for each cube in the column are required. This method of modeling 1-dimensional scenarios requires a significant amount of data storage and computation.

According to the present invention, some or all of the wrapping may be done in the Monte Carlo modeling of the cube. For instance, assume the coordinate system local to the 1-dimensional environment to be modeled is situated such that the optical parameters vary in the z direction and are constant in the x and y directions. Wrapping the Monte Carlo model in the y direction is equivalent to modeling, instead of a cube, an infinitely long bar with square cross section as shown in FIG. 5. The number of faces is therefore reduced from 6 to 4. And because the square grid cells become long strips, their number is reduced from 16 to 4. The square plates used for boundaries also become strips. If the directional resolution remains the same as before, the size of the RF for the bar is $((4\times4\times36\ 72)/2)^2=429,981,696$ data values, which is less than 3 percent of the former size discussed above.

These bars may be stacked vertically and the outputs in the x direction wrapped to model the 1-dimensional environment. To model a 2-dimensional scenario, an array of bars may be formed. A 3-dimensional model will require the original 3-dimensional cube to be modeled. Additionally, the Monte Carlo modeling of the bars is also performed in 3-dimensions.

ILLUSTRATIVE EXAMPLES AND TESTING OF THE EXAMPLES

Two model environments may are next presented to illustrate the methods and advantages of the present invention. A first example is a simple one-dimensional model representing a uniform water column, depicted in FIG. 6. The second example is a two-dimensional scenario in which a long barge floats over a uniform water column, as shown in FIG. 7. In the second example the bottom and sides of the barge were modeled as Lamberian reflectors with a reflectance of 0.1, and the right and left sides of the two-dimensional environment were wrapped in the above-described manner, creating a model environment representing a series of long parallel barges, each 10 m wide and spaced 20 meters apart. In both examples, the bottom and air/sea interface are flat and the water is 10 m deep. The sky for both cases consists of a direct beam at a zenith angle of 30° embedded in a uniform, diffuse background sky. The diffuse sky provides 21% of the downward irradiance.

Both environments were constructed using the 2-dimensional bars described above, each having 8 grid strips per face. The directional sphere was divided into 18 theta bins and 20 phi bins. The size of the RF for these bars is $((4\times8\times18\times20)^2=33,177,600$ data values, which, for double precision accuracy, requires about 265 MByte of data storage.

For each environment, two water types were modeled: one representing clear, offshore water, the other more turbid water characteristic of ports and estuaries, such as Tampa Bay. The optical parameters were set to match typical chlorophyll concentrations of 0.3 $mg/m^3$ and 5.0 $mg/m^3$, respectively. These readings are tabulated in Table 1, below. Additionally, both cases were simulated at a wavelength of 532 nm and the bottom reflectance was set to 0.15 for the clearer water and 0.05 for the more turbid estuarine water.

TABLE 1

Optical Parameters For Two Water Types, Wavelength = 532 nm

|  | Chl - 0.3 $mg/m^3$ | Chl - 5.0 $mg/m^3$ |
| --- | --- | --- |
| Absorption (water) | 0.05172 $m^{-1}$ | 0.05172 $m^{-1}$ |
| Scattering (water) | 0.00218 $m^{-1}$ | 0.00218 $m^{-1}$ |
| Absorption (particles and Colored Dissolved Organic Matter) | 0.01304 $m^{-1}$ | 0.1150 $m^{-1}$ |
| Scattering (particles) | 0.1448 $m^{-1}$ | 0.8391 $m^{-1}$ |
| Bottom reflectance | 0.15 | 0.05 |
| Barge reflectance | 0.10 | 0.10 |

One-Dimensional Example

Downward irradiance calculated by the hybrid model compares well with the Hydrolight results as shown in FIG. 8. The RMS difference between the two models for the clear water is 0.98%. For the turbid water, the difference is 2.36%. In both cases, the downward irradiance transmittance of the hybrid model is greater than that of Hydrolight.

Upward irradiance calculated by the hybrid model is comparable, but the difference in the two models is slightly increased: 1.28% RMS for the clear water, 3.63% for the turbid water as depicted in FIG. 9. Part of the difference in upward irradiance can be attributed to the difference in downward irradiance at the bottom. Even so, in this case the upward irradiance transmittance of the hybrid model is less than that of Hydrolight. Results shown in FIGS. 8 and 9 imply that the hybrid model may transport radiance preferentially depending on the direction of transport and the orientation of the model element. In this case, the direct solar beam may be transported more effectively than the diffuse radiance reflected from the bottom.

FIG. 10 shows the average cosines vs. the depth calculated by the two models. The upward average cosine is the average value of the polar angle of all the photons contributing to the upward irradiance at the given depth. The downward average cosine is defined analogously. The differences between the two models range from 1.40% RMS to 2.48% RMS, indicating that the subsurface radiance distributions generated by the two models are practically equivalent. Differences in the downward average cosines just beneath the surface may be related to differences in the way the two methods account for transmission and reflection at the interface.

The total upward radiance just above the surface in the half plane perpendicular to the principal plane is shown for both models and both water types in FIG. 11. The difference between the two models for the clear water is 7.36% RMS. For the turbid water, the difference is 8.94% RMS.

Several effects may contribute to the disparity between the two radiance distributions. First, in the present example the more than 33 million values defining the RF for the bar elements were derived in the Monte Carlo simulation from no more than 100 million weighted photon packages. The calculation of irradiances and average cosines requires the combination of the output values for many counting bins, thus smoothing occurs of the rough data resulting from the dearth of sample trajectories. Calculation of the radiance distributions combines fewer output values; so increased variance is expected. For example, the total upward irradiance just above the surface differs by only 2.25% for the two models for the clear water case, and this difference would likely be reduced if more photon packages were used to determine the RF for the bar elements. But even if this value is considered to be a systematic bias between the two models, simply increasing the number of photon packages used to determine the RF reduces the random errors in the radiance distributions to a comparable level.

Secondly, the differences shown in FIG. 11 represent the accumulation of all the errors in the hybrid model because the upward radiance distribution above surface relies on the transmission of the downward light from the source, through the air-sea interface, to the bottom of the water column, and then back. Therefore, the differences in the radiance distributions effectively represent the upper limit of the model error. Even so, the hybrid model results mimic the shape of the Hydrolight-produced radiance distribution quite well.

Finally, there are fundamental differences in the structure of the two models that make it difficult to formulate perfectly equivalent problems. Hydrolight uses the polar cap described above to combine all the bins above a zenith angle of 5°, and then partitions the remainder of the hemisphere down to 85° into 10° zonal bins centered at zenith angles of 10°, 20°, etc. The hybrid model, at the directional resolution used for this work, partitions the hemisphere into 10° zonal bins centered at zenith angles of 5°, 10°, etc. Thus, Hydrolight spreads the direct solar beam across a bin spanning from 25° to 35°, whereas the hybrid model spreads the beam across a bin spanning from 20° to 30°. This may account for the higher downward average cosine at the surface generated by the hybrid model, and also for the slightly higher downward irradiance transmittance.

There are also differences in the way the two models handle sub-surface internal reflection. The largest disparities in the radiance distributions shown in FIG. 11 occur for zenith angles greater than 75°, the portion of the distribution most affected by the subsurface internal-reflection algorithm. When data points corresponding to zenith angles greater man 75° are not considered, the RMS differences between radiance distributions generated by the two models for the clear and turbid water types drops from 7.36% RMS to 5.22% RMS and from 8.94% to 7.35%, respectively. Thus, so even within the Hydrolight model, use of finite bin sizes that don't precisely match and center about the geometry of the source and viewing angles will cause small discrepancies.

The above-surface radiance distributions should be axially symmetric when the sky conditions are changed for the model scenario so that the sun is at zenith with a uniform background sky. When the Hydrolight model is executed with a zenith sun, the resulting above-surface radiance distributions in the half-planes at 45° and 90° to the principle plane differ by 1.28% RMS and 1.19% RMS for the clear and turbid waters, respectively.

Two-Dimensional Example

FIG. 12 shows the normalized downward irradiance beneath and adjacent to a barge afloat in the clear water type. It is important to note that vertical and horizontal axes are plotted to different scales. Data for these plots (FIGS. 12-15) was calculated at an eighth-meter resolution, then smoothed to a spatial resolution of one meter for plotting. The vertical lines just below the bottom corners of the barge are plotting artifacts caused by the combination of this low spatial resolution and the high horizontal gradient of downward irradiance at the edges of the barge. The shadow that extends above the sea surface on the left side of the barge is clearly shown, as is the sharp horizontal gradient in downward irradiance at the lower right corner of the barge. The contours indicate that a submersible vehicle moving beneath the barge at a depth of four meters would encounter changes in downward irradiance of nearly three orders of magnitude. This downward irradiance diffuses beneath the barge to fill in the shadow, but at the same time, the downward irradiance at the bottom in the deepest part of the barge shadow is more than an order of magnitude less than in the open spaces adjacent to the barge. Curvature of the downward irradiance contours extends to the edges of the plot, indicating that the downward irradiance in the open areas between the barges is perturbed by the presence of the barges and shadows.

FIG. 13 shows the upward irradiance modeled for the same conditions prevailing for FIG. 12. Because most of the upward irradiance originates from reflection off the Lambertian bottom and is more diffuse than the downward irradiance, the structure in the upward irradiance seen at the bottom dissipates with height. Unlike the downward irradiance field, the upward irradiance is more uniform just beneath the barge than it is just above the bottom. It is noted that the upward irradiance curvature contours to the right of the barge. The upward irradiance reaches a maximum for each depth at about 28-29 meters on the horizontal scale indicating that for this combination of model geometry and optical parameters, the series of barges are spaced so closely that the upward irradiance at any point more than a few meters from the bottom is affected by the shadows of at least two barges.

FIGS. 14 and 15 show the results of the hybrid method when the turbid water parameters are modeled in the same geometry as for FIGS. 12 and 13. In this case, the downward irradiance reflected from the bottom of the barge is about four orders of magnitude less than the total downward irradiance at the surface. The shape of the downward irradiance field (FIG. 14) is similar to that shown in FIG. 12, except that the contours of FIG. 14 are closer together because of the increased attenuation of the turbid water. At the edges of the plot, the downward irradiance contours are approximately linear and parallel to the bottom, an indication that the downward irradiance in this region is not affected by the presence of the barges.

The upward irradiance field (FIG. 15), however, is quite different than that shown in FIG. 13. The vertical contours emanating from the bottom of the barge in FIG. 15 show that the gradient of upward irradiance just beneath the barge is horizontal. The bottom of the barge is illuminated solely from infilling of irradiance from the open areas between the barges, not by reflection from the bottom. Unlike the clear water case, the upward irradiance distribution in the center off the region between the barges appears to be unperturbed by the barges or their shadows. For both water types, the effect of the reflection of downward irradiance from the bright side of the barge is shown clearly by the upward irradiance contours.

Applications of the Methods of the Present Invention

Optical sensors typically work within limited ranges of radiance. In order to optimize sensor performance, it is necessary to define the range of radiance within which the sensor is expected to function. Special operating techniques for sensors which are deployed in widely varying light fields may be necessary. For example, the light field beneath the barge as shown in FIG. 14 is more than three orders of magnitude lower than it is at the sea surface. To compensate for such a range, an automatic gain control (AGC) may be used to allow a single sensor or camera on an autonomous underwater vehicle (AUV) or remotely operated vehicle (ROV) to be effective in both environments. Furthermore, if the field of view of a video camera included both the right side and bottom of the barge, as shown in FIG. 12, the camera will view portions of the barge that contrast by more than two orders of magnitude. The automatic gain control for the sensor will then adjust to a value that is far too insensitive for use in discriminating objects on the bottom of the barge. Only when the side of the barge is excluded from the field of view will the inspection of the barge bottom be feasible. Operational practices can be devised to avoid such problems, one method being the use of zoom lens adjustments to avoid bright pixels.

Because of the more reflective bottom and less turbid waters typical of an offshore environment, almost three times as much natural light is available to illuminate the bottom of a ship for imaging by video camera or other conventional passive imaging sensors in offshore waters as is available in an inshore environment. On the other hand, if a laser line scanner is employed to inspect the bottom of a ship during daylight, higher contrast for observing the laser line would be available beneath a ship in inshore water. The hybrid model can produce the estimates of the ambient light field needed to determine the optimal location and instrument to be used for hull inspection.

Inspection of ship hulls is time-consuming, and therefore expensive; the hull of a ship transports liquefied natural gas may span more than five acres. Even so, because the consequences of such a vessel exploding in port would be catastrophic, divers now take up to two weeks to inspect the hulls of such ships before allowing entry to ports such as Boston Harbor. Delays in making port due to the inspection process could be greatly reduced using optical systems presently being developed when mounted on AUVs and/or ROVs. The savings accrued by employing such systems to inspect a large vessel would be on the order of $100,000 to $250,000 for each day by which the inspection process was shortened.

To prepare the operators of such vehicles for inspections beneath ships in various environments, a preview of the environment should be available in order to optimize the range and observational parameters for best sensor performance. The hybrid model can be run a priori to provide good estimates of the optical environments to be expected for a wide range of conditions. Then, given contemporaneous values of the optical qualities of the water and natural light conditions acquired by remote sensing or instrumented buoys, be vehicle operator may quickly extract the optimal sensor parameters from a look-up table. The parameters measured include water conductivity, temperature, sun angle, cloudiness, depth, water turbidity and any other parameters, such as absorptional and scattering coefficients, as known to one of ordinary skill in the art that affect the transmission of light in the test medium.

The instant invention has been described in terms of an underwater environment but it is within the scope of the invention that any other environment may also be modeled. This includes, but is not limited to, human, other mammalian or other types of body, including marine life, reptiles, etc. In addition, other environments, such as subaerial mountainous settings as known to those of skill in the art may also be modeled as long as they have methods of optical measurement applied to them.

In summary, by use of the Monte Carlo and iterative techniques simulated solutions to the Radiative Transfer Equations in one-, two- and three-dimensions can be made. The optical environment to be modeled is first partitioned into contiguous elements. In the illustrative example described herein, the elements were cubes or infinitely long bars of square cross-section. For each type of element, the type being defined by the geometric shape of the element and the distribution of optically active elements within it, Monte Carlo techniques are used to determine the element's optical response function or RF. Once the RF is calculated for every type of element in the region, the elements are assembled (conceptually), and the boundary conditions are imposed. Boundary conditions are implemented using specialized elements with specified, constant output states to represent sources, and elements with analytically determined response functions to represent reflective surfaces and Fresnel interfaces. The outputs of the source elements are diffused iteratively throughout the model region until the output states of all elements change negligibly with further iteration. One-dimensional results of the hybrid model compare well with the widely used Hydrolight program, with the largest differences seen in the above-water total upward radiance distributions.

The advantages of the hybrid model are exemplified by simulation of the two-dimensional light field adjacent to and beneath a series of evenly spaced long barges. The model region was partitioned into long bars with one-meter square cross-sections. The sides of each bar were further divided into eight strips. Because the water in the model region was defined to be homogeneous, only two types of bar elements were necessary; one type each for the clear and turbid water simulations. The iterative part of the hybrid model method combined the bars and solved simultaneously for the radiance distribution at each strip on each face of every bar in the model region. In other words, the complete radiance distribution, with a directional resolution of 18 theta values for each of 20 phi values, was determined at about 5000 locations throughout the model region using only one Monte Carlo simulation for each of the two water types comprising the model environment.

By use of this hybrid model radiance estimates are sufficient to allow for sensor calibration as well as predictability of performance, as well as whether or not data collection is viable for any set of parameters. This enables ship hull and port facility inspection to be done by ROV and AUV systems, that otherwise would require more costly and time-consuming techniques. In addition, the methods of the present invention apply to systems wherein the instrumentation is located on a spacecraft or on any type of aircraft system, including piloted, autonomous, or semi-autonomous systems. Combinations of these systems are also contemplated within the scope of the instant invention, so that simultaneous monitoring from a plurality of locations is also possible.

Modification and variation can be made to the disclosed embodiment of the instant invention without departing from the scope of the invention as described. Those skilled in the art will appreciate that the applications of the present invention herein are varied, and that the invention is described in the preferred embodiment. Accordingly, additions and modifications can be made without departing from the principles of the invention. Particularly with respect to the claims it should be understood that changes may be made without departing from the essence of this invention. In this regard it is intended that such changes would still fall within the scope of the present invention. Therefore, this invention is not limited to the particular embodiments disclosed, but is intended to cover modifications within the spirit and scope of the present invention as defined in the appended claims.

What is claimed is:

1. A method of determining a radiance field in an optical environment, said method comprising the steps of:
    generating a model of the optical environment;
    partitioning the modeled, optical environment into discreet, contiguous regions; and
    applying Monte Carlo techniques to determine an optical response function for each region for which the optical response function cannot be analytically defined; and
    reporting the optical response function determined by application of the Monte Carlo techniques.

2. A method as set forth in claim 1 further comprising the step of combining the optical response function for each region.

3. A method as set forth in claim 2 wherein the step of combining the optical response function for each region comprises utilizing an output of one region as an input to a contiguous region.

4. A method as set forth in claim 2 further comprising the step of applying iterative relaxation techniques to determine the radiance field on a boundary and throughout the modeled, optical environment.

5. A method as set forth in claim 1 wherein the step of applying Monte Carlo techniques to each region comprises solving the Radiative Transfer Equation (RTE) for each region to obtain an end solution.

6. A method as set forth in claim 5 further comprising the step of calibrating data from an optical sensor in response to the end solution.

7. A method as set forth in claim 6 wherein the step of calibrating data comprises adjusting gain of the optical sensor in response to the end solution.

8. A method as set forth in claim 6 wherein the optical sensor is located on at least one of a remotely operated vehicle (ROV), an autonomous underwater vehicle (AUV), a piloted aircraft, an autonomous aircraft, a semi-autonomous aircraft, a piloted spacecraft, an autonomous spacecraft, and a semi-autonomous spacecraft.

9. A method as set forth in claim 5 further comprising the step of validating data from an optical sensor in response to the end solution.

10. A method as set forth in claim 9 wherein the optical sensor is located on at least one of a remotely operated vehicle (ROV), an autonomous underwater vehicle (AUV), a piloted aircraft, an autonomous aircraft, a semi-autonomous aircraft, a piloted spacecraft, an autonomous spacecraft, and a semi-autonomous spacecraft.

11. A method as set forth in claim 5 further comprising the step of determining an optical sensor to deploy in response to the end solution.

12. A method as set forth in claim 5 further comprising the step of adjusting an optical sensor in response to the end solution prior to deployment of the optical sensor.

13. A method as set forth in claim 1 wherein the optical environment is underwater.

14. A method as set forth in claim 1 wherein the optical environment is subaerial.

15. A program product for determining a radiance field in an optical environment wherein program product code is stored on computer readable media and comprises:
    a modeling code stored on the computer readable media for generating a model of the optical environment;
    a partitioning code stored on the computer readable media for partitioning the modeled, optical environment into discreet, contiguous regions; and
    an application code stored on the computer readable media for applying Monte Carlo techniques to determine an optical response function for each region for which the optical response function cannot be analytically defined.

16. A program product as set forth in claim 15 further comprising a combination code stored on the computer readable media for combining the optical response function for each region.

17. A program product as set forth in claim 16 further comprising a relaxation code stored on the computer readable media for applying iterative relaxation techniques to determine the radiance field on a boundary and throughout the modeled, optical environment.

* * * * *